United States Patent
Mecca et al.

(10) Patent No.: US 11,369,550 B2
(45) Date of Patent: Jun. 28, 2022

(54) TINTED MINERAL SUNSCREEN COMPOSITIONS

(71) Applicant: L'OREAL, Paris (FR)

(72) Inventors: Jaimie Mecca, Clifton, NJ (US); Jennifer Lynn Paulucci, Manalapan, NJ (US); Patricia Brieva, Manalapan, NJ (US); Anil Shah, Hamilton, NJ (US); Brian Bodnar, Manasquan, NJ (US); Rabia Ahmad, Clark, NJ (US)

(73) Assignee: L'OREAL, Paris (FR)

( * ) Notice: Subject to any disclaimer, the term of this patent is extended or adjusted under 35 U.S.C. 154(b) by 163 days.

(21) Appl. No.: 16/697,695

(22) Filed: Nov. 27, 2019

(65) Prior Publication Data
US 2021/0154106 A1 May 27, 2021

(51) Int. Cl.
*A61K 8/06* (2006.01)
*A61K 8/41* (2006.01)
*A61K 8/81* (2006.01)
*A61Q 17/04* (2006.01)
*A61K 8/19* (2006.01)

(52) U.S. Cl.
CPC ............... *A61K 8/064* (2013.01); *A61K 8/19* (2013.01); *A61K 8/416* (2013.01); *A61K 8/8141* (2013.01); *A61Q 17/04* (2013.01); *A61K 2800/43* (2013.01); *A61K 2800/48* (2013.01); *A61K 2800/612* (2013.01)

(58) Field of Classification Search
None
See application file for complete search history.

(56) References Cited

U.S. PATENT DOCUMENTS

| 8,241,613 | B2 | 8/2012 | Candau et al. | |
|---|---|---|---|---|
| 2002/0054890 | A1* | 5/2002 | Gers-Barlag | A61K 8/27 424/401 |
| 2006/0182770 | A1* | 8/2006 | Tanojo | A61P 17/06 424/400 |
| 2007/0248550 | A1* | 10/2007 | Patel | A61K 8/69 424/59 |
| 2007/0264204 | A1* | 11/2007 | Noor | A61Q 1/06 424/47 |
| 2010/0003290 | A1* | 1/2010 | Schlossman | A61K 8/69 424/401 |
| 2020/0138681 | A1 | 5/2020 | Shah et al. | |

FOREIGN PATENT DOCUMENTS

WO 2020/097233 5/2020

* cited by examiner

*Primary Examiner* — Aradhana Sasan
(74) *Attorney, Agent, or Firm* — Laetitia Leproust; Robert Klemz

(57) ABSTRACT

A tinted mineral sunscreen composition is provided in the form of a water-in-oil emulsion comprising a cationic surfactant; one or more oil thickening agent; one or more mineral pigments; one or more mineral UV filtering agents; and water wherein the ratio between the cationic surfactant and the total amount of oil thickening agents is from about 0.05 to about 3.

21 Claims, No Drawings

TINTED MINERAL SUNSCREEN COMPOSITIONS

FIELD OF THE DISCLOSURE

The instant disclosure is directed to sunscreen compositions, and to methods for using the sunscreen compositions to protect keratinous substrates such as skin and hair from UV radiation.

BACKGROUND

The negative effects of exposure to ultraviolet ("UV") light are well known. Prolonged exposure to sunlight causes damage such as sunburn to the skin and dries out hair making it brittle. When skin is exposed to UV light having a wavelength of from about 290 nm to about 400 nm, long term damage can lead to serious conditions such as skin cancer.

UV light also contributes to aging by causing free radicals to form in the skin. Free radicals include, for example, singlet oxygen, hydroxyl radical, the superoxide anion, nitric oxide and hydrogen radicals. Free radicals attack DNA, membrane lipids and proteins, generating carbon radicals. These in turn react with oxygen to produce a peroxyl radical that can attack adjacent fatty acids to generate new carbon radicals. This cascade leads to a chain reaction producing lipid peroxidation products. Damage to the cell membrane results in loss of cell permeability, increased intercellular ionic concentration, and decreased ability to excrete or detoxify waste products. The end result is a loss of skin elasticity and the appearance of wrinkles. This process is commonly referred to as photo-aging.

Sunscreens can be used to protect against UV damage and delay the signs of photo-aging. The degree of UV protection afforded by a sunscreen composition is directly related to the amount and type of UV filters contained therein. The higher the amount of UV filters, the greater the degree of UV protection. Nevertheless, it is desirable to achieve the best photo protection efficacy with the lowest amount of UV filters. In particular, it is especially desirable to achieve high photoprotection with the lowest amount of UV filters when formulating with mineral UV filtering agents, since mineral UV filtering agents also result in a white color when applied to the skin when higher amounts are used in cosmetic formulations. The inventors of the instant disclosure discovered ways to formulate a tinted mineral-based sunscreen with minimum or no whitening with good aesthetics and good efficacy.

SUMMARY OF THE INVENTION

The instant disclosure relates to sunscreen compositions which provide a high degree of sun protection and are aesthetically pleasing when applied to skin. The sunscreen compositions include mineral UV filtering agents, which are known to be non-irritating, natural, and gentle to the skin. One drawback with mineral-based sunscreen compositions is that they often appear white when applied to the skin. Consumers prefer sunscreen compositions to appear natural (unnoticeable). Developing mineral-based sunscreen products having a high Sun Protection Factor (SPF) that exhibit minimal or no whitening, however, is challenging, especially when such compositions also contain pigments.

The inventors of the instant case discovered a combination of ingredients within a certain ratio that improve the feeling, aesthetic and the stability of the compositions. The compositions in the form of a water-in-oil emulsion typically include:

a. From about 0.1 to about 3 wt. % of a cationic surfactant;
b. From about 0.5 to about 4 wt. % of one or more oil thickening agent;
c. From about 0.5 to about 4 wt. % of one or more mineral pigments;
d. One or more mineral UV filtering agents;
e. A water phase of about 28 to about 50 wt. % of water;

wherein the ratio between the cationic surfactant and the total amount of oil thickening agents is from about 0.05 to about 3; and wherein the weight percentages are based on the total weight of the composition.

In one or more embodiments, the sunscreen composition exhibits a high shear viscosity transition at or near skin temperature, thereby providing additional beneficial aesthetic properties for the user. In some embodiments, the sunscreen composition is free of silicone.

In some embodiments, the cationic surfactant is quaternary ammonium compound. In one or more embodiments, the quaternary ammonium compound contains one or two alkyl chains which independently have from about 14 to about 24 carbon atoms; and the quaternary ammonium compound has a cosmetically acceptable counter ion selected from chloride, bromide, and methosulfate. In some embodiments, the quaternary ammonium is chosen from cetrimonium chloride, cetrimonium methosulfate, stearimonium chloride, behentrimonium chloride, behentrimonium methosulfate, behenamidopropyltrimonium methosulfate, stearamidopropyltrimonium chloride, cetyltrimethylammonium chloride, cetyltrimethylammonium bromide, dipalmitoylethyl hydroxyethylmonium methosulfate, dicetyldimonium chloride, and mixtures thereof.

In one or more embodiments, the one or more oil thickening agents comprise polyalcohol acrylates. In some embodiments, the polyalcohol acrylate is a poly C10-30 alkyl acrylate. In some embodiments, the total amount of oil thickening agents is present from about 0.8 to about 3 wt. % based on the total weight of the composition.

In some embodiments, the one or more mineral pigments comprise a silicone treatment. In some embodiments, the one or more mineral pigments comprise non-silicone treated mineral pigments. In some embodiments, the one or more mineral pigment is surface-treated with a trialkoxyalkylsilane. In some embodiments, the mineral pigments comprise modified amino acid-treated pigments. In some embodiments, the modified amino acid-treated pigments comprise N-acyl-glutamine-treated pigments. In one or more embodiments, the inventive composition may comprise more than one mineral pigment, each of which has a different color.

In one or more embodiments, the one or more mineral pigment may comprise a metal oxide. In some embodiments, the one or more mineral pigment may comprise an iron oxide. In some embodiments, the iron oxide comprises yellow iron oxide, black iron oxide, red iron oxide or mixtures thereof.

In some embodiments, the one or more mineral UV filtering agents are selected from titanium dioxide, zinc oxide, iron oxides, cerium oxides, zirconium oxides, and mixtures thereof. In one or more embodiments, the one or more mineral UV filtering agents is present from about 1 to about 25 wt. % based on the total weight of the composition.

In some embodiments, the composition described in the instant disclosure may further comprise one or more fillers.

In some embodiments, the composition described in the instant disclosure may further comprise one or more emulsifiers. In some embodiments, the one or more emulsifiers are chosen from glyceryl esters and derivatives, and alkoxylated carboxylic acids, and mixtures thereof. In one embodiment, the emulsifier comprises a mixture of a glyceryl esters and alkoxylated carboxylic acids. In one embodiment, the one or more emulsifier is polyglyceryl-4 isostearate. In other embodiments, the one or more emulsifier is PEG-30 dipolyhydroxystearate. In one or more embodiments, the one or more emulsifiers are present from about 1 to about 10 wt. % by weight base on the total weight of the composition.

In some embodiments, the ratio between the cationic surfactant and the total amount of oil thickening agents is from about 0.05 to about 3.

In various embodiments, the composition described in the instant disclosure can further comprise an SPF booster. In one embodiment, the SPF booster is Diethylhexyl Syringylidenemalonate.

Another aspect of the instant disclosure can include:
a. From about 0.1 to about 3 wt. % of a cationic surfactant;
b. From about 0.5 to about 4 wt. % of one or more oil thickening agent;
c. From about 0.5 to about 4 wt. % of one or more non-silicone treated pigments
d. One or more mineral UV filtering agents;
e. One or more fillers;
f. A water phase of about 28 to about 45 wt. % of water;
wherein the ratio between the cationic surfactant and the total amount of oil thickening agents is from about 0.05 to about 3; and wherein the weight percentages are based on the total weight of the composition.

The instant disclosure also relates to methods for protecting skin from UV radiation comprising applying an effective amount of the sunscreen composition disclosed in the present case to the skin.

DETAILED DESCRIPTION OF THE DISCLOSURE

Where the following terms are used in this specification, they are used as defined below.

The terms "comprising," "having," and "including" are used in their open, non-limiting sense.

The terms "a" and "the" are understood to encompass the plural as well as the singular.

The term "mineral UV filtering agent" is interchangeable with the terms "mineral UV screening agent," "inorganic UV filtering agent," "inorganic UV screening agent," "mineral UV filter, and "inorganic UV filter." Mineral UV filtering agents are compounds that do not include any carbon atoms in their chemical structures that are capable of screening out, scattering, or absorbing UV radiation between 280 and 400 nm.

The term "water phase", defined herein, represents the sum total of all ingredients in the composition which are water-soluble or water-dispersible, and which are combined together with water during the preparation of the example emulsion compositions.

The compositions and methods of the instant disclosure can comprise, consist of, or consist essentially of the essential elements and limitations of the disclosure described herein, as well as any additional or optional ingredients, components, or limitations described herein or otherwise useful.

All percentages, parts and ratios herein are based upon the total weight of the compositions of the instant disclosure, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

Other than in the operating examples, or where otherwise indicated, all numbers expressing quantities of ingredients and/or reaction conditions are to be understood as being modified in all instances by the term "about," meaning within +/−5% of the indicated number.

As used herein, the expression "at least one" is interchangeable with the expression "one or more" and thus includes individual components as well as mixtures/combinations.

The term "treat" (and its grammatical variations) as used herein refers to the application of compositions of the instant disclosure onto the surface of skin and/or hair. The term 'treat" (and its grammatical variations) as used herein also refers to contacting the skin or hair with the compositions of the instant disclosure.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, less than 0.01 wt. %, or none of the specified material.

The term "active material" as used herein with respect to the percent amount of an ingredient or raw material, refers to 100% activity of the ingredient or raw material.

"Cosmetically acceptable" means that the item in question is compatible with a keratinous substrate such as skin and hair. For example, a "cosmetically acceptable carrier" means a carrier that is compatible with a keratinous substrate such as skin and hair.

"SPF booster" refers to a material which increases the UV absorption of another material when the two are intermixed in a composition by refracting UV radiation, thereby increasing the effective path length of the UV radiation through the composition. All SPF and UV-A ratings are provided on the basis of in-vivo value unless otherwise indicated.

The term, "a mixture thereof" or "mixtures thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included.

The salts referred to throughout the disclosure may include salts having a counter-ion such as an alkali metal, alkaline earth metal, or ammonium counter-ion. This list of counter-ions, however, is non-limiting.

The phrase "viscosity" refers to the thickness of a fluid or composition and is a measurement of a fluid or composition's resistance to flow. Herein, "viscosity" is synonymous to "dynamic viscosity" or "absolute viscosity", rather than "kinematic viscosity", and is measured by means of a rheometer in a method which is known to those skilled-in-the-art. Measurements of viscosity herein are reported in UD (Contraves units) unless otherwise specified.

The term "oil thickening agent" means any raw material which when combined with the oil phase of the emulsion results in a thickening action on said oil phase.

The term "aqueous phase" means water, water soluble, water miscible and water dispersible ingredients.

The expression "inclusive" for a range of concentrations means that the limits of the range are included in the defined interval.

The term "polymers," as defined herein, include homopolymers and copolymers formed from at least two different types of monomers.

The term "INCI" is an abbreviation of International Nomenclature of Cosmetic Ingredients, which is a system of names provided by the International Nomenclature Committee of the Personal Care Products Council to describe personal care ingredients.

The term "weight ratio" or "mass ratio" as used herein, references the amount of a substance in proportion to a mixture containing said substance, and is calculated by dividing the amount of said substance by weight contained in the mixture by the weight of the mixture containing said substance. As an example, a weight ratio of 0.4 for substance A in a mixture of A, B, and C indicates that the weight of substance A divided by the total weight of substances A, B, and C is 0.4.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

Some of the various categories of components identified may overlap. In such cases where overlap may exist and the composition includes both components (or the composition includes more than two components that overlap), an overlapping compound does not represent more than one component. For example, a fatty acid may be characterized as both a nonionic surfactant and a fatty compound. If a particular composition includes both a nonionic surfactant and a fatty compound, a single fatty acid will serve as only the nonionic surfactant or as only the fatty compound (the single fatty acid does not serve as both the nonionic surfactant and the fatty compound).

All publications and patent applications cited in this specification are herein incorporated by reference, and for any and all purposes, as if each individual publication or patent application were specifically and individually indicated to be incorporated by reference. In the event of an inconsistency between the instant disclosure and any publications or patent application incorporated herein by reference, the instant disclosure controls.

The instant disclosure relates to a sunscreen composition comprising a combination of ingredients within a certain ratio that improve the feeling, aesthetic and the stability of the compositions. The sunscreen compositions of the instant disclosure, in their broadest sense, is in the form of a water-in-oil emulsion and typically include:

a. From about 0.1 to about 3 wt. % of a cationic surfactant;
b. From about 0.5 to about 4 wt. % of one or more oil thickening agent;
c. From about 0.5 to about 4 wt. % of one or more mineral pigments;
d. One or more mineral UV filtering agents;
e. A water phase of about 28 to about 50 wt. % of water;
wherein the ratio between the cationic surfactant and the total amount of oil thickening agents is from about 0.05 to about 3; and
wherein the weight percentages are based on the total weight of the composition.

The sunscreen compositions of the instant disclosure surprisingly exhibit a great UV protection with mineral UV filtering agents without whitening, with a great sensorial on the skin and in which pigments were incorporated.

The sunscreen compositions are particularly unique in that they exhibit minimal or no whitening despite the presence of mineral UV filtering agents and a pleasing and aesthetic effect despite the fact that the compositions are free of silicone.

Without being bound by theory, it is believed that the presence of a cationic surfactant within a specific ratio of the total amount of oil thickening agents, together make the inventive compositions exhibit a very pleasing effect when applied as well as no whitening.

Cationic Surfactants

The cationic surfactant(s) may be selected from those known in the art. Non-limiting examples include quaternary ammonium-type cationic surfactants. In some instances, the cationic surfactant(s) may be selected from quaternary ammonium compounds containing one or two alkyl chains which independently have from about 14 to about 24 carbon atoms in each chain, and a counterion selected from chloride, bromide, and methosulfate (preferably methosulfate). Non-limiting examples include cetrimonium chloride, cetrimonium methosulfate, stearimonium chloride, behentrimonium chloride, behentrimonium methosulfate, behenamidopropyltrimonium methosulfate, stearamidopropyltrimonium chloride, cetyltrimethylammonium chloride, cetyltrimethylammonium bromide, dipalmitoylethyl hydroxyethylmonium methosulfate, dicetyldimonium chloride, and a mixture thereof.

The total amount of the cationic surfactant(s) in the compositions may be present in the composition in an amount from about 0.1, 0.12, 0.13, 0.14, 0.15, 0.16, 0.17, 0.18, 0.20, 0.22, 0.24, 0.26, 0.28, 0.30, 0.32, 0.34, 0.36, 0.38, 0.4, 0.45, 0.5, 0.55, 0.60, 0.65, 0.70, 0.75, 0.8, 0.85, 0.90, 0.95, 1.0 to about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 or 3 wt. % by weight percentages based on the total weight of the composition.

Oil Thickening agents

The total amount of oil thickening agent in the instant disclosure can vary, but is typically in the amount of about 0.5 to about 4 wt. % by weight percentages based on the total weight of composition. The total amount of oil thickening agents in the composition can vary but is typically from about 0.5, 0.6, 0.7, 0.8, 0.9, 1.0, 1.1, 1.2, 1.3, 1.4, 1.5, 1.6, 1.7, 1.8, 1.9, 2.0 to about 2.0, 2.1, 2.3, 2.4, 2.5, 2.6, 2.7, 2.8, 2.9, 3.0, 3.2, 3.4, 3.6, 3.8, or 4 wt. % by weight percentages based on the total weight of the composition.

The oil thickening agents used in the instant disclosure can be selected from semi-crystalline or crystalline polymers and/or semi-crystalline or crystalline waxes. It is preferable to adjust the total amount of oil thickening agent, the ratio of oil thickening agents, and the amount of water phase in order to maintain the desired viscosity of the composition.

(I) Semi-Crystalline or Crystalline Polymer

The semi-crystalline or crystalline polymer is preferably a semi-crystalline polymer. The term "semi-crystalline polymer" means polymers comprising a crystallizable portion, a crystallizable pendent and/or end chain or a crystallizable block in the backbone and/or at the ends, and an amorphous portion in the backbone, and having a first-order reversible temperature of change of phase, in particular of melting (solid-liquid transition). When the crystallizable portion is in the form of a crystallizable block of the polymer backbone, the amorphous portion of the polymer is in the form of an amorphous block; the semi-crystalline polymer is, in this case, a block copolymer, for example of the diblock, triblock or multiblock type, comprising at least one crystallizable block and at least one amorphous block. The term "block" generally means at least five identical repeating units. The crystallizable block(s) are then of different chemical nature from the amorphous block(s).

The semi-crystalline polymer according to the instant disclosure has a melting point of greater than or equal to 30° C., preferably ranging from 30° C. to 60° C., and in particular ranging from 40° C. to 50° C. This melting point is a first-order temperature of change of state.

This melting point may be measured by any known method and in particular using a differential scanning calorimeter (DSC), for example the calorimeter sold under the name DSC Q2000 by the company TA Instruments.

Advantageously, the semi-crystalline polymer(s) to which the instant disclosure applies has a number-average molecular mass of greater than or equal to 1000.

Advantageously, the semi-crystalline polymer(s) of the composition of the disclosure has a number-average molecular mass MN ranging from 2000 to 800 000, preferably from 3000 to 500 000, better still from 4000 to 150 000 and especially less than 100 000 and better still from 4000 to 99 000. Preferably, they have a number-average molecular mass of greater than 5600, for example ranging from 5700 to 99 000.

For the purposes of the instant disclosure, the expression "crystallizable chain or block" means a chain or block which, if it were obtained alone, would change from the amorphous state to the crystalline state reversibly, depending on whether the temperature is above or below the melting point. For the purposes of the instant disclosure, a "chain" is a group of atoms, which are pendent or lateral relative to the polymer backbone. A "block" is a group of atoms belonging to the backbone, this group constituting one of the repeating units of the polymer. Advantageously, the "pendent crystallizable chain" may be a chain containing at least 6 carbon atoms.

Preferably, the crystallizable block(s) or chain(s) of the semi-crystalline polymers represent at least 30% of the total weight of each polymer and better still at least 40%. The semi-crystalline polymers of the instant disclosure containing crystallizable blocks are block or multi-block polymers. They may be obtained via polymerization of a monomer containing reactive double bonds (or ethylenic bonds) or via polycondensation. When the polymers of the instant disclosure are polymers containing crystallizable side chains, these side chains are advantageously in random or statistical form.

Preferably, the semi-crystalline polymers that may be used in the composition according to the instant disclosure are of synthetic origin. Moreover, they do not comprise a polysaccharide backbone. In general, the crystallizable units (chains or blocks) of the semi-crystalline polymers according to the disclosure originate from monomer(s) containing crystallizable block(s) or chain(s), used for the manufacture of the semi-crystalline polymers.

According to the disclosure, the semi-crystalline polymer may be chosen from block copolymers comprising at least one crystallizable block and at least one amorphous block, and homopolymers and copolymers bearing at least one crystallizable side chain per repeating unit, and mixtures thereof.

The semi-crystalline polymers that may be used in the disclosure are in particular:
- block copolymers of polyolefins with controlled crystallization, especially those whose monomers are described in EP-A-0 951 897,
- polycondensates, especially of aliphatic or aromatic polyester type or of aliphatic/aromatic copolyester type,
- homopolymers or copolymers bearing at least one crystallizable side chain and homopolymers or copolymers bearing at least one crystallizable block in the backbone, for instance those described in document U.S. Pat. No. 5,156,911,
- homopolymers or copolymers bearing at least one crystallizable side chain, in particular containing fluoro group(s), as described in document WO-A-01/19333, and mixtures thereof.

In the last two cases, the crystallizable side chain(s) or block(s) are hydrophobic.

(i) Semi-Crystalline Polymers Containing Crystallizable Side Chains

Mention may be made in particular of those defined in documents U.S. Pat. No. 5,156,911 and WO-A-01/19333. They are homopolymers or copolymers comprising from 50% to 100% by weight of units resulting from the polymerization of one or more monomers bearing a crystallizable hydrophobic side chain.

These homopolymers or copolymers are of any nature, provided that they meet the conditions mentioned previously.

They can result:
- from the polymerization, especially the free-radical polymerization, of one or more monomers containing reactive double or ethylenic bond(s) with respect to a polymerization, namely a vinyl, (meth)acrylic or allylic group,
- from the polycondensation of one or more monomers bearing co-reactive groups (carboxylic acid, sulfonic acid, alcohol, amine or isocyanate), such as, for example, polyesters, polyurethanes, polyethers, polyureas or polyamides.

In general, these polymers are chosen especially from homopolymers and copolymers resulting from the polymerization of at least one monomer containing crystallizable chain(s) that may be represented by formula (I):

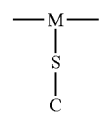

with M representing an atom of the polymer backbone, S representing a spacer and C representing a crystallizable group.

The crystallizable chains "—S—C" may be aliphatic or aromatic, and optionally fluorinated or perfluorinated. "S" especially represents the group (CH2)n or (CH2CH2O)n or (CH2O), which may be linear or branched or cyclic, with n being an integer ranging from 0 to 22. Preferably, "S" is a linear group. Preferably, "S" and "C" are different.

When the crystallizable chains "—S—C" are hydrocarbon-based aliphatic chains, they comprise hydrocarbon-based alkyl chains containing at least 11 carbon atoms and not more than 40 carbon atoms and better still not more than 24 carbon atoms. They are especially aliphatic chains or alkyl chains containing at least 12 carbon atoms, and they are preferably C14-C24 alkyl chains. When they are fluoroalkyl- or perfluoroalkyl-chains, they contain at least six fluorinated carbon atoms and especially at least 11 carbon atoms, at least six of which carbon atoms are fluorinated.

As examples of semi-crystalline polymers or copolymers bearing crystallizable chain(s), mention may be made of those resulting from the polymerization of one or more of the following monomers: (meth)acrylates of saturated alkyl with the alkyl group being C14-C24, perfluoroalkyl (meth) acrylates with a C11-C15 perfluoroalkyl group, N-alkyl (meth)acrylamides with the alkyl group being C14 to C24 with or without a fluorine atom, vinyl esters containing alkyl or perfluoro(alkyl) chains with the alkyl group being C14 to C24 (with at least 6 fluorine atoms per perfluoroalkyl chain), vinyl ethers containing alkyl or perfluoro(alkyl) chains with the alkyl group being C14 to C24 and at least 6 fluorine atoms per perfluoroalkyl chain, C14 to C24 alpha-olefins such as, for example, octadecene, para-alkylstyrenes with an alkyl group containing from 12 to 24 carbon atoms, and mixtures thereof.

When the polymers result from a polycondensation, the hydrocarbon-based and/or fluorinated crystallizable chains as defined above are borne by a monomer that may be a diacid, a diol, a diamine or a diisocyanate.

When the polymers that are the subject of the instant disclosure are copolymers, they additionally contain from 0 to 50% of groups Y or Z resulting from the copolymerization:

α) of Y which is a polar or non-polar monomer or a mixture of the two:

When Y is a polar monomer, it is either a monomer bearing polyoxyalkylenated groups (especially oxyethylenated and/or oxypropylenated groups), a hydroxyalkyl (meth)acrylate, for instance hydroxyethyl acrylate, (meth) acrylamide, an N-alkyl(meth)acrylamide, an N,N-dialkyl (meth)acrylamide such as, for example, N,N-diisopropylacrylamide or N-vinylpyrrolidone (NVP), N-vinylcaprolactam, a monomer bearing at least one carboxylic acid group, for instance (meth)acrylic acid, crotonic acid, itaconic acid, maleic acid or fumaric acid, or bearing a carboxylic acid anhydride group, for instance maleic anhydride, and mixtures thereof.

When Y is a non-polar monomer, it may be an ester of the linear, branched or cyclic alkyl (meth)acrylate type, a vinyl ester, an alkyl vinyl ether, an α-olefin, styrene or styrene substituted with a C1 to C10 alkyl group, for instance α-methylstyrene.

For the purposes of the instant disclosure, the term "alkyl" means a saturated group especially of C8 to C24, except where otherwise mentioned, and better still of C14 to C24.

β) of Z which is a polar monomer or a mixture of polar monomers. In this case, Z has the same definition as the "polar Y" defined above.

Preferably, the semi-crystalline polymers containing a crystallizable side chain are alkyl (meth)acrylate or alkyl (meth)acrylamide homopolymers with an alkyl group as defined above, and especially of C14-C24, copolymers of these monomers with a hydrophilic monomer preferably of different nature from (meth)acrylic acid, for instance N-vinylpyrrolidone or hydroxyethyl (meth)acrylate, and mixtures thereof.

(ii) Polymers Bearing in the Backbone at Least One Crystallizable Block

These polymers are especially block copolymers consisting of at least two blocks of different chemical nature, one of which is crystallizable.

The block polymers defined in patent U.S. Pat. No. 5,156,911 may be used;

Block copolymers of olefin or of cycloolefin containing a crystallizable chain, for instance those derived from the block polymerization of:

cyclobutene, cyclohexene, cyclooctene, norbornene (i.e. bicyclo(2,2,1)-2-heptene), 5-methylnorbornene, 5-ethylnorbornene, 5,6-dimethylnorbornene, 5,5,6-trimethylnorbornene, 5-ethylidenenorbornene, 5-phenylnorbornene, 5-benzylnorbornene, 5-vinylnorbornene, 1,4,5,8-dimethano-1,2,3,4,4a,5,8a-tetrahydronaphthalene, dicyclopentadiene, or mixtures thereof, with ethylene, propylene, 1-butene, 3-methyl-1-butene, 1-hexene, 4-methyl-1-pentene, 1-octene, 1-decene or 1-eicosene, or mixtures thereof.

and in particular copoly(ethylene/norbornene) blocks and (ethylene/propylene/ethylidene-norbornene) block terpolymers. Those resulting from the block copolymerization of at least two C2-C16, better still C2-C12 and even better still C4-C12 α-olefins such as those mentioned above and in particular block bipolymers of ethylene and of 1-octene may also be used.

The copolymers may be copolymers containing at least one crystallizable block, the copolymer residue being amorphous (at room temperature). These copolymers may also contain two crystallizable blocks of different chemical nature. The preferred copolymers are those that simultaneously contain at room temperature a crystallizable block and an amorphous block that are both hydrophobic and lipophilic, sequentially distributed; mention may be made, for example, of polymers containing one of the crystallizable blocks and one of the amorphous blocks below:

Block that is crystallizable by nature: a) of polyester type, for instance poly(alkylene terephthalate), b) of polyolefin type, for instance polyethylenes or polypropylenes.

Amorphous and lipophilic block, for instance amorphous polyolefins or copoly(olefin)s such as poly(isobutylene), hydrogenated polybutadiene or hydrogenated poly(isoprene).

As examples of such copolymers containing a crystallizable block and a separate amorphous block, mention may be made of:

α) poly(ε-caprolactone)-b-poly(butadiene) block copolymers, preferably used hydrogenated, such as those described in the article "Melting behaviour of poly(ε-caprolactone)-block-polybutadiene copolymers" from S. Nojima, Macromolecules, 32, 3727-3734 (1999), β) the hydrogenated block or multiblock poly(butylene terephthalate)-b-poly(isoprene) block copolymers cited in the article "Study of morphological and mechanical properties of PP/PBT" by B. Boutevin et al., Polymer Bulletin, 34, 117-123 (1995), γ) the poly(ethylene)-b-copoly(ethylene/propylene) block copolymers cited in the articles "Morphology of semicrystalline block copolymers of ethylene-(ethylene-alt-propylene)" by P. Rangarajan et al., Macromolecules, 26, 4640-4645 (1993) and "Polymer aggregates with crystalline cores:

the system poly(ethylene)poly(ethylene-propylene)" by P. Richter et al., Macromolecules, 30, 1053-1068 (1997).

δ) the poly(ethylene)-b-poly(ethylethylene) block copolymers mentioned in the general article "Crystallization in block copolymers" by I. W. Hamley, Advances in Polymer Science, vol. 148, 113-137 (1999).

The semicrystalline polymers in the composition of the instant disclosure may or may not be partially crosslinked, provided that the degree of crosslinking does not interfere with their dissolution or dispersion in the liquid fatty phase optionally present in the composition by heating above their melting point. It may then be a case of chemical crosslinking, by reaction with a multifunctional monomer during the polymerization. It may also be a case of physical crosslinking, which may then be due either to the establishment of bonds of hydrogen or dipolar type between groups borne by the polymer, for instance dipolar interactions between carboxylate ionomers, these interactions being in small amount and borne by the polymer backbone; or to a phase separation between the crystallizable blocks and the amorphous blocks, borne by the polymer.

Preferably, the semi-crystalline polymers of the composition according to the instant disclosure are not crosslinked.

According to one particular embodiment of the disclosure, the polymer is chosen from copolymers resulting from the polymerization of at least one monomer containing a crystallizable chain chosen from saturated C14 to C24 alkyl (meth)acrylates, C11 to C15 perfluoroalkyl (meth)acrylates, C14 to C24 N-alkyl(meth)-acrylamides with or without a fluorine atom, vinyl esters containing C14 to C24 alkyl or perfluoroalkyl chains, vinyl ethers containing C14 to C24 alkyl or perfluoroalkyl chains, C14 to C24 alpha-olefins, para-alkylstyrenes with an alkyl group containing from 12 to 24 carbon atoms, with at least one optionally fluorinated C1 to C10 monocarboxylic acid ester or amide, which may be represented by the following formula (ω):

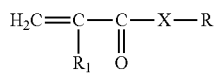

in which $R_1$ is H or $CH_3$, R represents an optionally fluorinated $C_1$-$C_{10}$ alkyl group and X represents O, NH or $NR_2$ in which $R_2$ represents an optionally fluorinated $C_1$-$C_{10}$ alkyl group.

According to one more particular embodiment of the instant disclosure, the polymer is derived from a monomer containing a crystallizable chain chosen from saturated C14 to C22 alkyl (meth)acrylates and even more particularly poly(stearyl acrylate) or poly(behenyl acrylate).

As particular examples of structuring semi-crystalline polymers that may be used in the composition according to the instant disclosure, mention may be made of polymers having the INCI name "Poly C10-C30 alkyl acrylate", for instance the Intelimer® products from the company Air Products, for instance the product Intelimer® IPA 13-1, which is a polystearyl acrylate and a melting point of 48° C. of a melting point, or the product Intelimer® IPA 13-6, which is a behenyl polymer.

The semi-crystalline polymers may especially be:
those described in Examples 3, 4, 5, 7, 9 and 13 of patent U.S. Pat. No. 5,156,911 containing a —COOH group, resulting from the copolymerization of acrylic acid and of C5 to C16 alkyl (meth)acrylate and more particularly of the copolymerization:

of acrylic acid, of hexadecyl acrylate and of isodecyl acrylate in a 1/16/3 weight ratio,
of acrylic acid and of pentadecyl acrylate in a 1/19 weight ratio,
of acrylic acid, of hexadecyl acrylate and of ethyl acrylate in a 2.5/76.5/20 weight ratio,
of acrylic acid, of hexadecyl acrylate and of methyl acrylate in a 5/85/10 weight ratio,
of acrylic acid and of octadecyl methacrylate in a 2.5/97.5 weight ratio,
of hexadecyl acrylate, of polyethylene glycol methacrylate monomethyl ether containing 8 ethylene glycol units, and of acrylic acid in an 8.5/1/0.5 weight ratio.

It is also possible to use the structure "O" from National Starch, as described in document U.S. Pat. No. 5,736,125, with a melting point of 44° C., and also semi-crystalline polymers with crystallizable pendent chains comprising fluoro groups, as described in Examples 1, 4, 6, 7 and 8 of document WO-A-01/19333.

It is also possible to use the semi-crystalline polymers obtained by copolymerization of stearyl acrylate and of acrylic acid or NVP as described in document U.S. Pat. No. 5,519,063 or EP-A-550 745, with melting points of 40° C. and 38° C., respectively.

It is also possible to use the semi-crystalline polymers obtained by copolymerization of behenyl acrylate and of acrylic acid or NVP, as described in documents U.S. Pat. No. 5,519,063 and EP-A-550 745, with melting points of 60° C. and 58° C., respectively.

Preferably, the semi-crystalline polymers do not comprise any carboxylic groups.

Finally, the semi-crystalline polymers according to the instant disclosure may also be chosen from waxy polymers obtained by metallocene catalysis, such as those described in patent application US 2007/0 031 361.

These polymers are homopolymers or copolymers of ethylene and/or propylene prepared via metallocene catalysis, i.e. by polymerization at low pressure and in the presence of a metallocene catalyst.

The weight-average molecular mass (Mw) of the waxes obtained via metallocene catalysis described in that document is less than or equal to 25 000 g/mol and ranges, for example, from 2000 to 22 000 g/mol and better still from 4000 to 20 000 g/mol.

The number-average molecular mass (Mn) of the waxes obtained via metallocene catalysis described in that document is preferably less than or equal to 15 000 g/mol and ranges, for example, from 1000 to 12 000 g/mol and better still from 2000 to 10 000 g/mol.

The polydispersity index I of the polymer is equal to the ratio of the weight-average molecular mass Mw to the number-average molecular mass Mn. Preferably, the polydispersity index of the waxy polymers is between 1.5 and 10, more preferably between 1.5 and 5, even more preferably between 1.5 and 3 and better still between 2 and 2.5.

The waxy homopolymers and copolymers may be obtained in a known manner from ethylene and/or propylene monomers, for example via metallocene catalysis according to the process described in document EP 571 882.

The homopolymers and copolymers of ethylene and/or propylene prepared via metallocene catalysis may be unmodified or "polar"-modified (polar-modified waxes, i.e. waxes modified such that they have the properties of a polar wax). The polar-modified waxy homopolymers and copolymers may be prepared in a known manner from unmodified waxy homopolymers and copolymers such as those described previously by oxidation with gases containing oxygen, such as air, or by grafting with polar monomers such as maleic acid or acrylic acid or alternatively derivatives of these acids. These two routes enabling polar modification of the polyolefins obtained via metallocene catalysis are described, respectively, in documents EP 890 583 and U.S. Pat. No. 5,998,547, for example, the content of these two documents being incorporated herein by reference.

According to the instant disclosure, the polar-modified homopolymers and copolymers of ethylene and/or propylene prepared via metallocene catalysis that are particularly preferred are polymers modified such that they have hydrophilic properties. Examples that may be mentioned include ethylene and/or propylene homopolymers or copolymers modified by the presence of hydrophilic groups such as maleic anhydride, acrylate, methacrylate, polyvinylpyrrolidone (PVP), etc.

Waxy ethylene and/or propylene homopolymers or copolymers modified by the presence of hydrophilic groups such as maleic anhydride or acrylate are particularly preferred.

Examples that may be mentioned include:
polypropylene waxes modified with maleic anhydride (PPMA) sold by the company Clariant, or polypropylene-ethylene-maleic anhydride copolymers, such as those sold by the company Clariant under the name LicoCare, for instance LicoCare PP207 LP3349, LicoCare CM401 LP3345, LicoCare CA301 LP3346 and LicoCare CA302 LP3347 or alternatively
the unmodified polyethylene waxes sold by the company Clariant, such as the product LicoCare PE 102 LP3329.

(II) Semi-Crystalline or Crystalline Wax

Semi-crystalline or crystalline waxes are chosen from polar and apolar hydrocarbon-based waxes, or mixtures thereof.

The term "wax(es)", under consideration in the context of the instant disclosure are generally lipophilic compounds that are solid at room temperature (25° C.), with a solid/liquid reversible change of state, having a melting point of greater than or equal to 30° C., which may be up to 200° C. and especially up to 120° C.

In particular, the semi-crystalline or crystalline waxes that are suitable for the instant disclosure may have a melting point of greater than or equal to 40° C., and less than or equal to 60° C. Furthermore, the semi-crystalline or crystalline waxes that are suitable for the instant disclosure may have a melting point of less than or equal to 100° C., preferably less than or equal to 85° C., and especially less than or equal to 70° C.

The semi-crystalline or crystalline waxes used in the instant disclosure can be semi-crystalline or crystalline apolar or polar wax.

(i) Apolar Wax

For the purposes of the instant disclosure, the term "apolar wax" means a wax whose solubility parameter at 25° C. as defined below, $\delta a$, is equal to 0 $(J/cm3)^{1/2}$.

Apolar waxes are in particular hydrocarbon-based waxes constituted solely of carbon and hydrogen atoms, and free of heteroatoms such as N, O, Si and P.

The term "hydrocarbon-based wax" means a wax formed essentially from, or even constituted of, carbon and hydrogen atoms, and optionally oxygen and nitrogen atoms, and not containing any silicon or fluorine atoms. It may contain alcohol, ester, ether, carboxylic acid, amine and/or amide groups.

The definition and calculation of the solubility parameters in the Hansen three-dimensional solubility space are described in the article by C. M. Hansen: The three-dimensional solubility parameters, J. Paint Technol. 39, 105 (1967).

According to this Hansen space:
$\delta D$ characterizes the London dispersion forces derived from the formation of dipoles induced during molecular impacts;
$\delta p$ characterizes the Debye interaction forces between permanent dipoles and also the Keesom interaction forces between induced dipoles and permanent dipoles;
$\delta h$ characterizes the specific interaction forces (such as hydrogen bonding, acid/base, donor/acceptor, etc.); and
$\delta a$ is determined by the equation: $\delta a = (\delta p^2 + \delta h^2)^{1/2}$ The parameters $\delta p$, $\delta h$, $\delta D$ and $\delta a$ are expressed in $(J/cm3)^{1/2}$.

More particularly, the apolar wax may be chosen from microcrystalline waxes, paraffin waxes, ozokerite, polyethylene waxes, polymethylene waxes and microwaxes, and mixtures thereof.

As microcrystalline waxes that may be used, mention may be made of Multiwax W 445® sold by the company Sonneborn, and Microwax HW® and Base Wax 30540® sold by the company Paramelt.

An ozokerite that may be mentioned is Ozokerite Wax SP 1020 P.

Polyethylene waxes that may be mentioned include Performalene 500-L Polyethylene and Performalene 400 Polyethylene sold by New Phase Technologies.

Polymethylene waxes that may be mentioned include the Polymethylene Wax sold under the reference Cirebelle 303, which has a melting point of 61° C. to 67° C.; and the Polymethylene Wax sold under the reference Cirebelle 108, which has a melting point of 79° C. to 84° C., sold by Cirebelle.

As microwaxes that may be used in the compositions according to the instant disclosure as apolar wax, mention may be made especially of polyethylene microwaxes such as those sold under the names Micropoly 200®, 220®, 220L® and 250S® by the company Micro Powders.

(ii) Polar Wax

For the purposes of the instant disclosure, the term "polar wax" means a wax whose solubility parameter at 25° C., $\delta a$, is other than 0 $(J/cm3)^{1/2}$.

The term "polar wax" here means a wax whose chemical structure is formed essentially from, or even constituted of, carbon and hydrogen atoms, and comprising at least one highly electronegative heteroatom such as an oxygen, nitrogen, silicon or phosphorus atom.

As the hydrocarbon-based polar wax, a wax chosen from ester waxes is in particular preferred.

The term "hydrocarbon-based" means a compound formed essentially from, or even constituted of, carbon and hydrogen atoms, and optionally oxygen and nitrogen atoms, and not containing any silicon or fluorine atoms.

According to the instant disclosure, the term "ester wax" means a wax comprising at least one ester function.

The following may especially be used as the ester wax:
ester waxes such as those chosen from:
i) waxes of formula R1COOR2 in which R1 and R2 represent linear, branched or cyclic aliphatic chains in which the number of atoms ranges from 10 to 50, which may contain a heteroatom such as O, N or P and whose melting point ranges from 25 to 120° C.

In particular, use may be made, as the ester wax, of a C20-C40 alkyl (hydroxystearyloxy)stearate (the alkyl group comprising from 20 to 40 carbon atoms), alone or as a mixture, or a C20-C40 alkyl stearate. Such waxes are especially sold under the names Kester Wax K 82 P®, Hydroxypolyester K 82 P®, Kester Wax K 80 P® and Kester Wax K82H by the company Koster Keunen.

ii) glycol and butylene glycol montanate (octacosanoate) waxes such as the wax Licowax KPS Flakes (INCI name: glycol montanate) sold by the company Clariant.

iii) bis(1,1,1-trimethylolpropane) tetrastearate, sold under the name Hest 2T-45® by the company Heterene.

iv) diester waxes of a dicarboxylic acid of general formula R3-(—OCO—R4-COO—R5), in which R3 and R5 are identical or different, preferably identical and represent a C4-C30 alkyl group (alkyl group comprising from 4 to 30 carbon atoms) and R4 represents a linear or branched C4-C30 aliphatic group (alkyl group comprising from 4 to 30 carbon atoms) which may or may not contain one or more unsaturated groups, and preferably that is linear and unsaturated.

v) Mention may also be made of the waxes obtained by catalytic hydrogenation of animal or plant oils having linear or branched C8-C32 fatty chains, for example such as hydrogenated jojoba oil, hydrogenated sunflower oil, hydrogenated castor oil, hydrogenated coconut oil, and also the waxes obtained by hydrogenation of castor oil esterified with cetyl alcohol, such as those sold under the names Phytowax Ricin 16L64® and 22L73® by the company Sophim. Such waxes are described in patent application FR-A-2792190 and the waxes obtained by hydrogenation of olive oil esterified with stearyl alcohol such as that sold under the name Phytowax Olive 18 L 57, or the like.

v) beeswax, synthetic beeswax, polyglycerolated beeswax, carnauba wax, candelilla wax, oxypropylenated lanolin wax, rice bran wax, ouricury wax, esparto grass wax, cork fibre wax, sugar cane wax, Japan wax, sumach wax, montan wax, orange wax, and laurel wax.

Mineral Pigments

In accordance with the instant disclosure, compositions comprising one or more mineral surface-treated pigment are provided. "Surface-treated pigment" means pigments that have partially undergone a surface treatment of chemical, electronic, electrochemical, mechanochemical or mechanical nature, with a surface treatment agent. Preferably, the pigments are selected from inorganic pigments or inorganic/organic mixed pigments.

In accordance with the instant disclosure, surface treatment agents are selected from the group consisting of alkyl silanes, organotitanates, halogenated phosphonates, halogenated organosilanes, and modified amino acids. According to preferred embodiments, pigments have been surface treated with a surface treatment agent selected from the group consisting of alkoxylated alkyl silanes such as, for example, ethoxylated and/or propoxylated C2-C8 alkyl silanes, and salts thereof, organotitanates such as, for example, titanium salts of fatty acids such as, for example, C2-C8 alkylated titanium salts of C9-C24 fatty acids such as stearic acid, isostearic acid, oleic acid, cetearic acid, cetyl acid, etc., halogenated organophosphonates such as, for example, perfluoroalkyl phosphonates, and salts thereof, and halogenated organosilanes such as, for example, perfluoro C2-C8 alkyl silanes (optionally ethoxylated and/or propoxylated), and salts thereof. In other preferred embodiments, pigments have been surface treated with a surface treatment agent selected from a group of modified amino acids such as disodium stearoyl glutamate. Specific examples of suitable surface treatment agents include (1) triethoxy caprylylsilane, (2) perfluorooctyltriethoxysilane, (3) sodium perfluorohexylethylphosphonate, (4) isopropyl titanium triisosterate, and (4) disodium stearoyl glutamate.

Preferred surface treatment agents are selected from the group consisting of alkyl silanes, halogenated organosilanes, and modified amino acids.

The surface-treated pigments of the instant disclosure can be prepared according to surface treatment techniques well known to a person of ordinary skill in the art or can be found commercially.

For example, the surface treatment agent with which the pigments are treated can be deposited on the pigments by solvent evaporation, chemical reaction between the molecules of the surface treatment agent or creation of a covalent bond between the surface treatment agent and the pigments. The surface treatment can thus be carried out, for example, by chemical reaction of a surface treatment agent with the surface of the pigments and creation of a covalent bond between the surface treatment agent and the pigments. An exemplary method is described, for example, in U.S. Pat. No. 4,578,266, the entire contents of which is hereby incorporated by reference.

The surface-treated pigment preferably is present in the compositions of the instant disclosure in an active solid content amount ranging from about 0.5% to about 4 wt. % by weight percentages based on the total weight of the composition.

According to one or more embodiments of the instant disclosure, the compositions comprise one or more mineral pigment, wherein the pigment is surface-treated with a trialkoxyalkylsilane (e.g., trimethoxycaprylylsilane or triethoxycaprylylsilane). Such colored compositions can be cosmetic compositions such as, for example, lip compositions, foundations or eye shadows.

Suppliers for the surface-treated pigments are available from Kobo, Daito Kasei, Gelest, Sensient, and Miyoshi.

In one or more embodiments, the composition further comprises more than one pigment. The additional pigments may be untreated, provided that they remain stable in the composition. In some embodiments, the composition further comprises an untreated mineral pigment.

In one or more embodiments, the pigment comprises a metal oxide (which is surface-treated with a trialkoxyalkylsilane). In further embodiments, the metal oxide comprises iron oxide, titanium dioxide, zinc oxide, chromium oxide or combinations thereof.

In alternative embodiments, the pigment comprises a metal sulfide (which is surface-treated with a trialkoxyalkylsilane). In further embodiments, the metal sulfide comprises ultramarine blue.

Representative examples of mineral pigments include titanium dioxide, zirconium oxide, zinc oxide, cerium oxide, iron oxides, chromium oxides, manganese violet, ultramarine blue, chromium hydrate, and ferric blue ferric ammonium ferrocyanide, fluorphlogopite, etc. Representative examples of organic pigments include carbon black, pigments of D & C type, and lakes based on cochineal carmine, barium, strontium, calcium, and aluminum.

Representative examples of inorganic pigments useful in the instant disclosure include those selected from the group consisting of rutile or anatase titanium dioxide, coded in the Color Index under the reference CI 77,891; black, yellow, red and brown iron oxides, coded under references CI 77,499, 77,492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

Representative examples of organic pigments and lakes useful in the instant disclosure include, but are not limited to, D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430) and the dye or lakes based on cochineal carmine (CI 75,570) and mixtures thereof.

The one or more mineral pigments may be present in the composition in a concentration ranging from about 0.5, 0.6, 0.7, 0.8, 0.9, 1.0, 1.1, 1.2, 1.3, 1.4, 1.5, 1.6, 1.7, 1.8, 1.9, 2.0 to about 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9 or 4 wt. % by weight percentages based on the total weight of the composition. In embodiments where there is more than one pigment present in the composition, the above amounts refer to the total amount of pigment.

Mineral UV Filtering Agents

In some embodiments, the one or more mineral UV filtering agents are selected from titanium dioxide, zinc oxide, iron oxides, cerium oxides, zirconium oxides, and a mixture thereof. In some embodiments, the one or more mineral UV filtering agents is present from about 1% to about 25 wt. %, based on the total weight of the sunscreen composition. The total amount of mineral UV filtering agents in the mineral sunscreen compositions can vary but is typically from about 1%, 2%, 3%, 4%, 5%, 6%, 7%, 8%, 9%, 10%, 11%, 12%, 13%, 14% to about 14%, 15%, 16%, 17%, 18%, 19%, 20%, 21%, 22%, 23%, 24%, or 25%.

Non-limiting examples of mineral UV filtering agent include treated or untreated metal oxides such as, for example, pigments or nanopigments of titanium oxide (amorphous or crystallized in rutile and/or anatase form), of iron oxide, of zinc oxide, of zirconium oxide or of cerium oxide. Particularly preferred mineral UV filtering agents include titanium dioxide and/or zinc oxide.

In some instances, the mean particle size may be about 5 nm to about 25 µm, about 10 nm to about 10 µm, or about 15 nm to about 5 µm. The mineral UV filtering agents may be nano-pigments having a mean particle size of about 5 nm to about 100 nm, about 5 nm to about 75 nm, or about 10 nm to 50 nm. Larger particles sizes may also be useful, for example about 1 µm to about 25 µm, about 5 µm to about 20 µm, or about 10 µm to about 15 µm.

Treated mineral UV filtering agents are mineral UV filtering agents that have undergone one or more surface treatments of chemical, electronic, mechanochemical and/or mechanical nature with compounds as described, for example, in Cosmetics & Toiletries, February 1990, Vol. 105, pp. 53-64, such as amino acids, beeswax, fatty acids, fatty alcohols, anionic surfactants, lecithins, sodium, potassium, zinc, iron or aluminium salts of fatty acids, metal (titanium or aluminium) alkoxides, polyethylene, silicones, proteins (collagen or elastin), alkanolamines, silicon oxides, metal oxides, sodium hexametaphosphate, alumina or glycerol.

The treated mineral UV filtering agents may be titanium oxides treated with:

silica and alumina, such as the products "Micro titanium Dioxide MT 500 SA" and "Microtitanium Dioxide MT 100 SA" from the company Tayca, and the products "Tioveil Fin", "Tioveil OP", "Tioveil MOTG" and "Tioveil IPM" from the company Tioxide;

alumina and aluminium stearate, such as the product "Microtitanium Dioxide MT 100 T" from the company Tayca;

alumina and aluminium laurate, such as the product "Microtitanium Dioxide MT 100 S" from the company Tayca;

iron oxides and iron stearate, such as the product "Microtitanium Dioxide MT 100 F" from the company Tayca;

silica, alumina and silicone, such as the products "Microtitanium Dioxide MT 100 SAS", "Microtitanium Dioxide MT 600 SAS" and "Microtitanium Dioxide MT 500 SAS" from the company Tayca;

sodium hexametaphosphate, such as the product "Microtitanium Dioxide MT 150 W" from the company Tayca;

octyltrimethoxysilane, such as the product "T-805" from the company Degussa;

alumina and stearic acid, such as the product "UVT M160" from the company Kemira;

alumina and glycerol, such as the product "UVT-M212" from the company Kemira;

alumina and silicone, such as the product "UVT-M262" from the company Kemira.

Other titanium oxide mineral UV filtering agents treated with a silicone are TiO2 treated with octyltrimethylsilane and for which the mean size of the elementary particles is between 25 and 40 nm, such as the product sold under the trade name "T805" by the company Degussa Silices, TiO2 treated with a polydimethylsiloxane and for which the mean size of the elementary particles is 21 nm, such as the product sold under the trade name "70250 Cardre UF TiO2SI3" by the company Cardre, anatase/rutile TiO2 treated with a polydimethylhydrogenosiloxane and for which the mean size of the elementary particles is 25 nm, such as the product sold under the trade name "Microtitanium Dioxide USP Grade Hydrophobic" by the company Color Techniques.

Uncoated titanium oxide mineral UV filtering agents are sold, for example, by the company Tayca under the trade names "Microtitanium Dioxide MT 500 B" or "Microtitanium Dioxide MT 600 B", by the company Degussa under the name "P 25", by the company Wackher under the name "Oxyde de titane transparent PW", by the company Myoshi Kasei under the name "UFTR", by the company Tomen under the name "ITS" and by the company Tioxide under the name "Tioveil AQ".

The uncoated zinc oxide mineral UV filtering agents are, for example:

those sold under the name "Nanox" by the company Elementis; and those sold under the name "Nanogard WCD 2025" by the company Nanophase Technologies.

The coated zinc oxide mineral UV filtering agents are, for example:

those sold under the name "Zinc Oxide CS-5" by the company Toshibi (ZnO coated with polymethylhydrogenosiloxane);

those sold under the name "Z-cote" by the company BASF, coated with triethoxycaprylylsilane;

those sold under the name "Nanogard Zinc Oxide FN" by the company Nanophase Technologies (as a 40% dispersion in Finsolv TN, C12-C15 alkyl benzoate);

those sold under the name "Daitopersion ZN-30" and "Daitopersion ZN-50" by the company Daito (dispersions in cyclopolymethylsiloxane/oxyethylenated polydimethyksiloxane, containing 30% or 50% of nanozinc oxides coated with silica and polymethylhydrogenosiloxane);

those sold under the name "NFD Ultrafine ZNO" by the company Daikin (ZnO coated with perfluoroalkyl phosphate and copolymer based on perfluoroalkylethyl as a dispersion in cyclopentasiloxane);

those sold under the name "SPD-Z1" by the company Shin-Etsu (ZnO coated with silicone-grafted acrylic polymer, dispersed in cyclodimethylsiloxane);

those sold under the name "Escalol Z100" by the company ISP (alumina-treated ZnO dispersed in an ethylhexyl methoxycinnamate/PVP-hexadecene/methicone copolymer mixture);

those sold under the name "Fuji ZNO-SMS-10" by the company Fuji Pigment (ZnO coated with silica and polymethylsilsesquioxane); and those sold under the name "Nanox Gel TN" by the company Elementis (ZnO dispersed at a concentration of 55% in C12-C15 alkyl benzoate with hydroxystearic acid polycondensate).

The uncoated cerium oxide mineral UV filtering agents are sold under the name "Colloidal Cerium Oxide" by the company Rhone-Poulenc. The uncoated iron oxide nanopigments are sold, for example, by the company Arnaud under the names "Nanogard WCD 2002 (FE 45B)", "Nanogard Iron FE 45 BL AQ", "Nanogard FE 45R AQ" and "Nanogard WCD 2006 (FE 45R)" or by the company Mitsubishi under the name "TY-220". The coated iron oxide nanopigments are sold, for example, by the company Arnaud under the names "Nanogard WCD 2008 (FE 45B FN)", "Nanogard WCD 2009 (FE 45B 556)", "Nanogard FE 45 BL 345" and "Nanogard FE 45 BL" or by the company BASF under the name "Transparent Iron Oxide".

Mixtures of metal oxides may also be used, especially of titanium dioxide and of cerium dioxide, including the silica-coated equal-weight mixture of titanium dioxide and of cerium dioxide, sold by the company Ikeda under the name "Sunveil A", and also the alumina, silica and silicone-coated mixture of titanium dioxide and of zinc dioxide, such as the product "M 261" sold by the company Kemira, or the alumina, silica and glycerol-coated mixture of titanium dioxide and of zinc dioxide, such as the product "M 211" sold by the company Kemira.

The composition may further include SPF boosters.

The total amount of mineral UV filtering agents in the mineral sunscreen compositions can vary but is typically from about 1%, 2%, 3%, 4%, 5%, 6%, 7%, 8%, 9%, 10%, 11%, 12%, 13%, 14% to about 14%, 15%, 16%, 17%, 18%, 19%, 20%, 21%, 22%, 23%, 24%, or 25% based on the total weight of the composition.

Emollients/Oils

The oil may be selected from the group consisting of oils of plant or animal origin, synthetic oils, silicone oils, hydrocarbon oils and fatty alcohols.

As examples of plant oils, mention may be made of, for example, linseed oil, camellia oil, macadamia nut oil, corn oil, mink oil, olive oil, avocado oil, sasanqua oil, castor oil, safflower oil, sunflower oil, almond oil, rapeseed oil, sesame oil, soybean oil, peanut oil, and mixtures thereof.

As examples of animal oils, mention may be made of, for example, squalene and squalane.

As examples of synthetic oils, mention may be made of alkane oils such as isododecane and isohexadecane, ester oils, ether oils, and artificial triglycerides.

The ester oils are preferably liquid esters of saturated or unsaturated, linear or branched C1-C26 aliphatic monoacids or polyacids and of saturated or unsaturated, linear or branched C1-C26 aliphatic monoalcohols or polyalcohols, the total number of carbon atoms of the esters being greater than or equal to 10.

Preferably, for the esters of monoalcohols, at least one from among the alcohol and the acid from which the esters of the instant disclosure are derived is branched.

Among the monoesters of monoacids and of monoalcohols, mention may be made of ethyl palmitate, ethyl hexyl palmitate, isopropyl palmitate, dicaprylyl carbonate, alkyl myristates such as isopropyl myristate or ethyl myristate, isocetyl stearate, 2-ethylhexyl isononanoate, isononyl isononanoate, isodecyl neopentanoate, and isostearyl neopentanoate.

Esters of C4-C22 dicarboxylic or tricarboxylic acids and of C1-C22 alcohols, and esters of monocarboxylic, dicarboxylic, or tricarboxylic acids and of non-sugar C4-C26 dihydroxy, trihydroxy, tetrahydroxy, or pentahydroxy alcohols may also be used.

Mention may especially be made of: diethyl sebacate; isopropyl lauroyl sarcosinate; diisopropyl sebacate; bis(2-ethylhexyl) sebacate; diisopropyl adipate; di-n-propyl adipate; dioctyl adipate; bis(2-ethylhexyl) adipate; diisostearyl adipate; bis(2-ethylhexyl) maleate; triisopropyl citrate; triisocetyl citrate; triisostearyl citrate; glyceryl trilactate; glyceryl trioctanoate; trioctyldodecyl citrate; trioleyl citrate; neopentyl glycol diheptanoate; diethylene glycol diisononanoate.

As ester oils, one can use sugar esters and diesters of C6-C30 and preferably C12-C22 fatty acids. It is recalled that the term "sugar" means oxygen-bearing hydrocarbon-based compounds containing several alcohol functions, with or without aldehyde or ketone functions, and which comprise at least 4 carbon atoms. These sugars may be monosaccharides, oligosaccharides, or polysaccharides.

Examples of suitable sugars that may be mentioned include sucrose (or saccharose), glucose, galactose, ribose, fucose, maltose, fructose, mannose, arabinose, xylose, and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated C6-C30 and preferably C12-C22 fatty acids. If they are unsaturated, these compounds may have one to three conjugated or non-conjugated carbon-carbon double bonds.

The esters according to this variant may also be selected from monoesters, diesters, triesters, tetraesters, and polyesters, and mixtures thereof.

These esters may be, for example, oleates, laurates, palmitates, myristates, behenates, cocoates, stearates, linoleates, linolenates, caprates, and arachidonates, or mixtures thereof such as, especially, oleopalmitate, oleostearate, and palmitostearate mixed esters, as well as pentaerythrityl tetraethyl hexanoate.

More particularly, use is made of monoesters and diesters and especially sucrose, glucose, or methylglucose monooleates or dioleates, stearates, behenates, oleopalmitates, linoleates, linolenates, and oleostearates.

An example that may be mentioned is the product sold under the name Glucate® DO by the company Amerchol, which is a methylglucose dioleate.

As examples of preferable ester oils, mention may be made of, for example, diisopropyl adipate, dioctyl adipate, 2-ethylhexyl hexanoate, ethyl laurate, cetyl octanoate, octyldodecyl octanoate, isodecyl neopentanoate, myristyl propionate, 2-ethylhexyl 2-ethylhexanoate, 2-ethylhexyl octanoate, 2-ethylhexyl caprylate/caprate, methyl palmitate, ethyl palmitate, isopropyl palmitate, dicaprylyl carbonate, isopropyl lauroyl sarcosinate, isononyl isononanoate, ethylhexyl palmitate, isohexyl laurate, hexyl laurate, isocetyl stearate, isopropyl isostearate, isopropyl myristate, isodecyl oleate, glyceryl tri(2-ethylhexanoate), pentaerythrithyl tetra(2-ethylhexanoate), 2-ethylhexyl succinate, diethyl sebacate, and mixtures thereof.

As examples of ether oils, mention may be made of, for example, ether oils with a short hydrocarbon chain or chains, such as dicaprylyl ether.

As examples of artificial triglycerides, mention may be made of, for example, capryl caprylyl glycerides, glyceryl trimyristate, glyceryl tripalmitate, glyceryl trilinolenate, glyceryl trilaurate, glyceryl tricaprate, glyceryl tricaprylate, glyceryl tri(caprate/caprylate), and glyceryl tri(caprate/caprylate/linolenate).

Emulsifiers

The sunscreen compositions may optionally include one or more emulsifiers such as an amphoteric, anionic, cationic or nonionic emulsifier, used alone or as a mixture, and optionally a co-emulsifier. Emulsifiers are most often used when the sunscreen composition is in the form of an emulsion. The emulsifiers are chosen in an appropriate manner according to the emulsion to be obtained (W/O or O/W).

For W/O emulsions, examples of emulsifiers that may be mentioned include dimethicone copolyols, such as the mixture of cyclomethicone and dimethicone copolyol sold under the trade name DC 5225 C by the company Dow Corning, and alkyl dimethicone copolyols such as the lauryl dimethicone copolyol sold under the name Dow Corning 5200 Formulation Aid by the company Dow Corning, and the cetyl dimethicone copolyol sold under the name Abil EM 90™ by the company Goldschmidt. A crosslinked elastomeric solid organopolysiloxane comprising at least one oxyalkylene group, such as those obtained according to the procedure of Examples 3, 4 and 8 of U.S. Pat. No. 5,412,004 and of the examples of U.S. Pat. No. 5,811,487, especially the product of Example 3 (synthesis example) of U.S. Pat. No. 5,412,004, such as the product sold under the reference KSG 21 by the company Shin-Etsu, may also be used as surfactants for W/O emulsions.

For O/W emulsions, examples of emulsifiers that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alcohol ethers; sugar esters such as sucrose stearate; and mixtures thereof.

The fatty acid esters of a sugar that can be used as nonionic amphiphilic lipids can be chosen in particular from the group comprising esters or mixtures of esters of a C8-C22 fatty acid and of sucrose, of maltose, of glucose or of fructose, and esters or mixtures of esters of a C14-C22 fatty acid and of methylglucose.

The C8-C22 or C14-C22 fatty acids forming the fatty unit of the esters that can be used in the emulsion comprise a saturated or unsaturated linear alkyl chain having, respectively, from 8 to 22 or from 14 to 22 carbon atoms. The fatty unit of the esters can be chosen in particular from stearates, behenates, arachidonates, palmitates, myristates, laurates, caprates and mixtures thereof.

By way of example of esters or of mixtures of esters of a fatty acid and of sucrose, of maltose, of glucose or of fructose, mention may be made of sucrose monostearte, sucrose distearate, sucrose tristearate and mixtures thereof, such as the products sold by the company Croda under the name Crodesta F50, F70, F110 and F160 having, respectively, an HLB (Hydrophilic Lipophilic Balance) of 5, 7, 11 and 16; and, by way of example of esters or of mixtures of esters of a fatty acid and of methylglucose, mention may be made of the disearate of methylglucose and of polyglycerol-3, sold by the company Goldschmidt under the name Tegocare 450. Mention may also be made of glucose monoesters or maltose monoesters, such as methyl O-hexadecanoyl-6-D-glucoside and O-hexadecanoyl-6-D-maltoside.

The fatty alcohol ethers of a sugar that can be used as nonionic amphiphilic lipids can be chosen in particular form the group comprising ethers or mixtures of ethers of a C8-C22 fatty alcohol and of glucose, of maltose, of sucrose or of fructose, and ethers or mixtures of ethers of a C14-C22 fatty alcohol and of methylglucose. They are in particular alkylpolyglucosides.

The C8-C22 or C14-C22 fatty alcohols forming the fatty unit of the ethers that can be used in the emulsion of the instant disclosure comprise a saturated or unsaturated linear alkyl chain having, respectively, from 8 to 22 or from 14 to 22 carbon atoms. The fatty unit of the ethers can be chosen in particular from decyl, cetyl, behenyl, arachidyl, stearyl, palmityl, myristyl, lauryl, capryl and hexadecanoyl units, and mixtures thereof such as cetearyl.

By way of example of fatty alcohol ethers of a sugar, mention may be made of alkylpolyglucosides, such as decylglucoside and laurylglucoside sold, for example, by the company Henkel under the respective names Plantaren 2000 and Plantaren 1200, cetostearylglucoside, optionally as a mixture with cetostearyl alcohol, sold, for example, under the name Montanov 68 by the company Seppic, under the name Tego-care CG90 by the company Goldschmidt and under the name Emulgade KE3302 by the company Henkel, and also arachidylglucoside, for example in the form of the mixture of arachidyl and behenyl alcohols and of arachidylglucoside sold under the name Montanov 202 by the company Seppic.

Use is more particularly made, as nonionic amphiphilic lipid of this type, of sucrose monostearate, sucrose distearate, sucrose tristearate and mixtures thereof, the distearate of methylglucose and of polyglycerol-3, and alkylpolyglucosides.

The glycerol fatty esters that can be used as nonionic amphiphilic lipids can be chosen in particular from the group comprising the esters formed from at least one acid comprising a saturated linear alkyl chain having from 16 to 22 carbon atoms, and from 1 to 10 glycerol units. Use may be made of one or more of these glycerol fatty esters in the emulsion of the instant disclosure.

These esters may be chosen in particular from stearates, behenates, arachidates, palmitates and mixtures thereof. Stearates and palmitates are preferably used.

By way of example of a surfactant that can be used in the emulsion of the instant disclosure, mention may be made of decaglycerol monostearate, distearate, tristearate and pentastearate (10 glycerol units) (CTFA names: polyglyceryl-10 stearate, polyglyceryl-10 distearate, polyglyceryl-10 tristearate, polyglyceryl-10 pentastearate), such as the products sold under the respective names Nikkol Decaglyn 1-S, 2-S, 3-S and 5-S by the company Nikko, and diglyceryl monostearate (CTFA name: polyglyceryl-2 stearate) such as the product sold by the company Nikko under the name Nikkol DGMS.

The sorbitan fatty esters that can be used as nonionic amphiphilic lipids chosen in particular from the group comprising esters of a C16-C22 fatty acid and of sorbitan and oxyethylenated esters of a C16-C22 fatty acid and of sorbitan. They are formed from at least one fatty acid comprising at least one saturated linear alkyl chain, having, respectively, from 16 to 22 carbon atoms, and from sorbitol or from ethoxylated sorbitol. The oxyethylenated esters generally comprise from 1 to 100 ethylene oxide units, and preferably from 2 to 40 ethylene oxide (EO) units.

These esters can be chosen in particular from stearates, behenates, arachidates, palmitates and mixtures thereof. Stearates and palmitates are preferably used.

By way of example of sorbitan fatty ester and of an oxyethylenated sorbitan fatty ester, mention may be made of sorbitan monostearate (CTFA name: sorbitan stearate) sold by the company ICI under the name Span 60, sorbitan monopalmitate (CTFA name: sorbitan palmitate) sold by the company ICI under the name Span 40, or sorbitan 20 EO tristearate (CTFA name: polysorbate 65) sold by the company ICI under the name Tween 65.

The ethoxylated fatty ethers are typically ethers made up of 1 to 100 ethylene oxide units and of at least one fatty alcohol chain having from 16 to 22 carbon atoms. The fatty chain of the ethers can be chosen in particular from behenyl, arachidyl, stearyl and cetyl units, and mixtures thereof, such as cetearyl. By way of example of ethoxylated fatty ethers, mention may be made of ethers of behenyl alcohol comprising 5, 10, 20 and 30 ethylene oxide units (CTFA names: beheneth-5, beheneth-10, beheneth-20 and beheneth-30), such as the products sold under the names Nikkol BBS, BB10, BB20 and BB30 by the company Nikko, and the ether of stearyl alcohol comprising 2 ethylene oxide units (CTFA name: steareth-2), such as the product sold under the name Brij 72 by the company ICI.

The ethoxylated fatty esters that can be used as nonionic amphiphilic lipids are esters made up of 1 to 100 ethylene oxide units and of at least one fatty acid chain comprising from 16 to 22 carbon atoms. The fatty chain of the esters can be chosen in particular from stearate, behenate, arachidate and palmitate units, and mixtures thereof. By way of example of ethoxylated fatty esters, mention may be made of the ester of stearic acid comprising 40 ethylene oxide units, such as the product sold under the name Myrj 52 (CTFA name: PEG-40 stearate) by the company ICI, and the ester of behenic acid comprising 8 ethylene oxide units (CTFA name: PEG-8 behenate), such as the product sold under the name Compritol HD5 ATO by the company Gattefosse.

The block copolymers of ethylene oxide and of propylene oxide that can be used as nonionic amphiphilic can be chosen in particular from poloxamers and in particular from Poloxamer 231, such as the product sold by the company ICI under the name Pluronic L81 of formula (V) with x=z=6, y=39 (HLB 2); Poloxamer 282, such as the product sold by the company ICI under the name Pluronic L92 of formula (V) with x=z=10, y=47 (HLB 6); and Poloxamer 124, such as the product sold by the company ICI under the name Pluronic L44 of formula (V) with x=z=11, y=21 (HLB 16).

As nonionic amphiphilic lipids, mention may also be made of the mixtures of nonionic surfactants described in document EP-A-705593, incorporated herein for reference.

Suitable hydrophobically-modified emulsifiers include, for example, inulin lauryl carbamate, commercially available from Beneo Orafti under the tradename Inutec SP1.

The total amount of emulsifiers in the sunscreen compositions, if present, may vary but are typically about 0.1 to about 30 wt. %, based on the total weight of the sunscreen composition. In some instances, the total amount of emulsifiers is about 0.1 to about 20 wt. %, about 0.1 to about 15 wt. %, about 0.1 to about 10 wt. %, about 0.5 to about 30 wt. %, about 0.5 to about 20 wt. %, about 0.5 to about 15 wt. %, about 0.5 to about 10 wt. %, about 1 to about 30 wt. %, about 1 to about 20 wt. %, about 1 to about 15 wt. %, about 1 to about 10 wt. %, or about 5 to about 5 wt. %, based on the total weight of the sunscreen composition.

Ratio

As mentioned previously, in some embodiments, the ratio between the cationic surfactant and the total amount of oil thickening agents is from about 0.05 to about 3.

The ratio between the cationic surfactant and the total amount of oil thickening agents may be in the amount from about 0.05, 0.06, 0.07, 0.08, 0.09, 0.1, 0.40, 0.42, 0.44, 0.46, 0.48, 0.5, 0.52, 0.54, 0.56, 0.58, 0.60, 0.62, 0.64, 0.66, 0.68, 0.70, 0.75, 0.8, 0.85, 0.90, 1, 1.2, 1.4, 1.6, 1.8, 2.0, 2.2, 2.4, 2.6, 2.8, or 3.0.

Boosters

The term "SPF booster" means a compound or composition that when used in a formulation in conjunction with a UV screening agent, increases the SPF of the formulation without increasing the amount of UV screening agent in the formulation. An example SPF booster capable of reflecting UV light is glass microspheres. Typically, the glass microspheres used in the compositions of the invention are essentially homogeneous and essentially uniform in sphericity and have a mean particle size of between about 5 .mu.m and 70 .mu.m, such as from about 10 .mu.m to 20 .mu.m. Glass microspheres useful in the present invention include hollow microspheres of calcium aluminum borosilicate (commercially available from Presperse Inc. under the trade name LUKSIL®), sodium borosilicate particulates (commercially available from PQ Corporation under the trade name Q-CEL 570), calcium/sodium borosilicate hollow microspheres (commercially available from 3M under the trade names ES 22 and 1 K), calcium/sodium borosilicate microspheres (commercially available from 3M's under the trade name Scotchlite™ K.sub.20 product).

Among other boosters, the compositions of the instant disclosure may further include, but not limited to, diethylhexyl syringylidenemalonate (formula I).

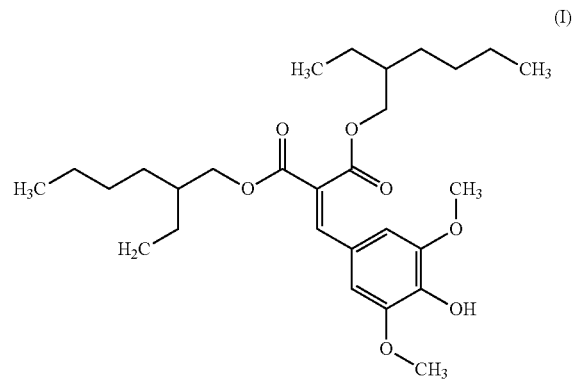 [SMILES: CCCCC(CC)COC(=O)C(=Cc1cc(OC)c(O)c(OC)c1)C(=O)OCC(CC)CCCC]

(I)

Fillers

A composition in accordance with the instant disclosure may comprise one or more filler of organic or mineral nature.

The term "filler" should be understood to mean colourless or white solid particles of any shape which are in a form that is insoluble and dispersed in the medium of the composition. They are mineral or organic in nature and make it possible to confer softness and mattness on the composition and a uniform makeup result.

The fillers used in the compositions according to the present invention may be in lamellar, globular or spherical form, in the form of fibers or in any other intermediate form between these defined forms.

The fillers according to the instant disclosure may or may not be surface-coated, and in particular they may be surface-treated with silicones, amino acids, fluoro derivatives or any other substance that promotes the dispersion and compatibility of the filler in the composition.

Among the mineral fillers that can be used in the compositions according to the instant disclosure, mention may be made of talc, mica, trimethyl siloxysilicate, kaolin, bentone, calcium carbonate, magnesium hydrogen carbonate, hydroxyapatite, boron nitride, perlite, glass or ceramic microcapsules, and mixtures thereof.

Among the organic fillers that can be used in the compositions according to the instant disclosure, mention may be made of polyamide powders (Nylon® Orgasol from Atochem), poly-.beta.-alanine and polyethylene powders, polytetrafluoroethylene (Teflon® from DuPont) powders, lauroyllysine, starch, modified or unmodified, specially oxidized ester modified starch, such as acetylated oxidized starch sold under the tradename GF-A390 by the company Suzhou Gaofeng, tetrafluoroethylene polymer powders, hollow polymer microspheres, such as Expancel (Nobel Industrie), metal soaps derived from organic carboxylic acids containing from 8 to 22 carbon atoms, preferably from 12 to 18 carbon atoms, for example zinc stearate, magnesium stearate or lithium stearate, zinc laurate, magnesium myristate, Polypore® L 200 (Chemdal Corporation), silicone resin microbeads (Tospearl® from Toshiba, for example), polyurethane powders, in particular powders of crosslinked polyurethane comprising a copolymer, said copolymer comprising trimethylol hexyllactone, for instance the hexamethylene diisocyanate/trimethylol hexyllactone polymer sold under the name Plastic Powder D-400® or Plastic Powder D-800® by the company Toshiki, carnauba microwaxes, such as the product sold under the name MicroCare 350® by the company Micro Powders, microwaxes of synthetic wax, such as the product sold under the name MicroEase 114S® by the company Micro Powders, microwaxes constituted of a mixture of carnauba wax and of polyethylene wax, such as those sold under the names MicroCare 300® and 310® by the company Micro Powders, microwaxes constituted of a mixture of carnauba wax and of synthetic wax, such as the product sold under the name MicroCare 325® by the company Micro Powders, polyethylene microwaxes, such as those sold under the names Micropoly 200®, 220®, 220L® and 250S® by the company Micro Powders; and mixtures thereof.

Advantageously, the filler suitable for the composition of the present invention is Ethylene/Acrylic Acid Copolymer.

Preferably, the one or more filler is present in the composition of the present invention from 0 to 20% by weight, preferably from 0.01% to 10%, more preferably from 0.1% to 5% by weight, relative to the total weight of the composition.

Cosmetically Acceptable Carrier

The sunscreen compositions include a cosmetically acceptable carrier. The phrase "cosmetically acceptable" means that the material is compatible with skin and hair. For example, "cosmetically acceptable carrier" means a carrier that is compatible with skin and hair, and is acceptable for application to the body.

The cosmetically acceptable carrier may include, for example, water and/or water soluble solvents. Non-limiting examples of cosmetically acceptable carriers include glycerin, C1-4 alcohols, organic solvents, fatty alcohols, fatty ethers, fatty esters, polyols, glycols, vegetable oils, mineral oils, liposomes, laminar lipid materials, water, or any combinations thereof.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

In some instances, cosmetically acceptable carriers may comprise water, a mixture of water and at least one cosmetically acceptable organic solvent, or at least one cosmetically acceptable organic solvent. Additionally, cosmetically acceptable carriers may be or may include ethanol, a glycol ether, for example, dipropylene glycol n-butyl ether, isododecane, mineral oil, propylene glycol, pentylene glycol, hexylene glycol, glycerol, and mixtures thereof.

Active Agents

Sunscreen compositions according to the instant disclosure can optionally further include active agents. Suitable active agents include, for example, anti-acne agents, antimicrobial agents, anti-inflammatory agents, analgesics, antierythemal agents, antiruritic agents, antiedermal agents, antipsoriatic agents, antifungal agents, skin protectants, vitamins, antioxidants, scavengers, antiirritants, antibacterial agents, antiviral agents, antiaging agents, protoprotection agents, hair growth enhancers, hair growth inhibitors, hair removal agents, antidandruff agents, anti-seborrheic agents, exfoliating agents, wound healing agents, anti-ectoparacitic agents, sebum modulators, immunomodulators, hormones, botanicals, moisturizers, astringents, cleansers, sensates, antibiotics, anesthetics, steroids, tissue healing substances, tissue regenerating substances, hydroxyalkyl urea, amino acids, peptides, minerals, ceramides, biohyaluronic acids, vitamins, skin lightening agents, self-tanning agents, coenzyme Q10, niacinimide, capcasin, caffeine, and any combination of any of the foregoing.

Adjuvants

Sunscreen compositions according to the instant disclosure can optionally include one or more adjuvants, such as pH adjusters, emollients, humectants, fillers, conditioning agents, moisturizers, chelating agents, propellants, rheology modifiers and emulsifiers such as gelling agents, colorants, fragrances, odor masking agents, UV stabilizer, preservatives, and any combination of any of the foregoing. Examples of pH adjusters include, but are not limited to, aminomethyl propanol, aminomethylpropane diol, triethanolamine, triethylamine, citric acid, sodium hydroxide, acetic acid, potassium hydroxide, lactic acid, and any combination thereof.

Suitable conditioning agents include, but are not limited to, cyclomethicone; petrolatum; dimethicone; dimethiconol; silicone, such as cyclopentasiloxane and diisostearoyl trimethylolpropane siloxy silicate; sodium hyaluronate; isopropyl palmitate; soybean oil; linoleic acid; PPG-12/saturated methylene diphenyldiisocyanate copolymer; urea; amodimethicone; trideceth-12; cekimonium chloride; diphenyl dimethicone; propylene glycol; glycerin; hydroxyalkyl urea; tocopherol; quaternary amines; and any combination thereof.

Suitable preservatives include, but are not limited to, chlorophenesin, sorbic acid, disodium ethylenedinitrilotetraacetate, phenoxyethanol, methylparaben, ethylparaben, propylparaben, phytic acid, imidazolidinyl urea, sodium dehydroacetate, benzyl alcohol, methylehloroisothiazolinone, methylisothiazolinone, and any combination thereof.

The instant disclosure also relates to methods for protecting skin from UV radiation comprising applying an effective amount of the sunscreen composition of claim 1 to the skin.

EXAMPLES

The following Examples are provided for illustrative purposes only, and are not intended to be limiting.

Example 1

TABLE 1

Table 1: Inventive Examples

| Claims | Phase | | Inci Us | Inventive Ex. 1* | Comparative Ex. 1* |
|---|---|---|---|---|---|
| (a) | B1 | Cationic Surfactant | Behentrimonium Methosulfate | 0.25 | 0 |
| (b) | B1 | Oil Thickening Agents | Poly C10-30 Alkyl Acrylate | 1.0 | 1 |
| | | Total Oil Thickening Agents | | 1.0 | 1.0 |
| (c) | B3 | Mineral Pigments | Iron Oxides | 0.8 | 0.8 |
| (d) | B2 | Mineral UV Filtering Agents | Titanium Dioxide (and) Aluminum Hydroxide (and) Stearic Acid | 0.82 | 0.82 |
| | | | Titanium Dioxide (and) Isohexadecane (and) Triethylhexanoin (and) Aluminum Stearate (and) Alumina (and) Polyhydroxystearic Acid | 4.7 | 4.7 |
| | | | Zinc Oxide (and) Triethoxycaprylylsilane | 9.9 | 9.9 |
| | | Filler | Ethylene/Acrylic Acid Copolymer | 1.5 | 1.5 |
| | A2 | Polymer | Xanthan Gum; Carbomer | 0.1 | 0.1 |
| | A1 | Preservatives | Chlorphenesin; Phenoxyyethanol; Salicylic Acid | ~0.8 | ~0.8 |
| | B1 | Water miscible Solvent | Caprylyl Glycol; C12-15 Alkyl Benzoate; Cetearyl Alcohol | ~1.3 | ~1.3 |
| | B1 | Emulsifiers | PEG-30 Dipolyhydroxystearate Polyglyceryl-4 Isostearate | 6.7 | 6.7 |
| | A1 | Ph Adjuster | Citric Acid Salicylic Acid | ~1 | ~1 |
| | A1 | Water | Water | QS | QS |

*= % represents the % of Active Raw Material

The following procedure was used to prepare both the comparative and inventive examples above.

1. Into the annex kettle, water, pH adjuster as needed, preservatives and Xanthan Gum were added to Phase A and mix. The kettle was heated until about 70 C.
2. In the primary kettle, the oil-soluble ingredients, C12-15 Alkyl Benzoate, Isohexadecane, PEG-30 Dipolyhydroxystearate, Polyglyceryl-4 Isostearate, Behentrimonium Methosulfate, the mineral UV filters, C10-30 Alkyl Acrylate, and the Iron oxide pigments were combined. The primary kettle was then started heating to 70 C. It was then mixed with a turbine once the raw materials were melted, and with adequate mixing where needed in between ingredients.
3. Once homogeneous Phase A was added to the primary kettle.
4. Once homogeneous, it was cooled down to ambient temperature.
5. Ethylene/Acrylic Acid Copolymer was added and mixed until homogeneous.

The comparative examples presented in Table 1 were prepared according to the procedure described above.

Viscosity Measurement

The viscosity of the inventive examples was measured using a rotational viscometer (Model R 180 Rheomat). The R 180 Rheomat is a rotational viscometer that uses a motor driven bob (or spindle) that rotates within a fixed cylinder, which allows for a defined geometry. The shear resistance of the sample in the gap allows for the measurement of motor torque.

TABLE 2

| Formula | Viscosity (UD unit*) |
|---|---|
| Inventive Ex. 1 | 66 UD |
| Comparative Ex. 1 | 40 UD |

*= UD is in Contraves units

The procedure described above was used. The viscosities were then derived knowing the shear rate and motor torque (shear stress).

Results

According to the data collected for the inventive and comparative examples, it is apparent that the presence of the cationic surfactant and one or more oil thickening agents within a certain ratio are correlated to the viscosity and, as such, the stability of the inventive compositions. The combination of the amount of oil thickening agents, the ratio of oil thickening agents, and amount of water phase define the examples which fit the summary of the instant disclosure, and which allow for one skilled-in-the-art to prepare compositions which have a suitable viscosity in order to exhibit the aesthetically-pleasing qualities described in the present case.

In the inventive example, when the total amount of oil thickening agent was about 1.0%, where the total water phase was about 20% to about 60% and where the amount of cationic surfactant was about 0.25%. In order to obtain a stable and acceptable viscosity, the viscosity measured should be between 52 and 72 UD. In our case, the Inventive Example 1 exhibited a viscosity of 66 UD which is in the range expected. However, the Comparative Example 1 exhibited a viscosity of 40 UD and was out of the range expected.

This was not the case for the comparative examples. These two examples demonstrate that the combination of oil thickening agents with the cationic surfactant is needed to obtain a viscosity that would also provide stability to the compositions.

While the disclosure has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A composition in the form of a water-in-oil emulsion comprising:
   a. from about 0.1 to about 3 wt. % of a cationic surfactant;
   b. from about 0.5 to about 4 wt. % of one or more oil thickening agents;
   c. from about 0.5 to about 4 wt. % of one or more mineral pigments;
   d. one or more mineral UV filtering agents;
   e. a water phase of about 28 to about 50 wt. % of water;
   f. one or more emulsifiers; and
      wherein the ratio between the cationic surfactant and the total amount of oil thickening agents is from about 0.05 to about 3; and
      wherein the weight percentages are based on the total weight of the composition.

2. The composition of claim 1, wherein the cationic surfactant is a quaternary ammonium compound.

3. The composition of claim 2, wherein the quaternary ammonium compound contains one or two alkyl chains which independently have from about 14 to about 24 carbon atoms; and the quaternary ammonium compound has a cosmetically acceptable counterion selected from chloride, bromide, and methosulfate.

4. The composition of claim 3 comprising cetrimonium chloride, cetrimonium methosulfate, stearimonium chloride, behentrimonium chloride, behentrimonium methosulfate, behenamidopropyltrimonium methosulfate, stearamidopropyltrimonium chloride, cetyltrimethylammonium chloride, cetyltrimethylammonium bromide, dipalmitoylethyl hydroxyethylmonium methosulfate, dicetyldimonium chloride, and a mixture thereof.

5. The composition of claim 1, wherein the one or more oil thickening agents comprises polyalcohol acrylates.

6. The composition of claim 5, wherein the polyalcohol acrylate is a poly C10-30 alkyl acrylate.

7. The composition of claim 1, wherein the total amount of oil thickening agents is present from about 0.8 to about 3 wt. % based on the total weight of the composition.

8. The composition of claim 1, wherein the one or more mineral pigments comprises a silicone treatment.

9. The composition of claim 1, wherein the one or more mineral pigments comprises non-silicone treated pigments.

10. The composition of claim 1, wherein the one or mineral pigment is surface-treated with a trialkoxyalkylsilane.

11. The composition of claim 1, wherein the one or mineral pigments comprises modified amino acid-treated pigments.

12. The composition of claim 11, wherein the modified amino acid-treated pigments comprise N-acyl-glutamine-treated pigments.

13. The composition of claim 1, comprises more than one mineral pigment, each of which has a different color.

14. The composition of claim 1, wherein the one or more mineral pigment comprises a metal oxide.

15. The composition of claim 14, wherein the metal oxide comprises an iron oxide.

16. The composition of claim 15, wherein iron oxide comprises yellow iron oxide, black iron oxide, red iron oxide or a mixture thereof.

17. The composition of claim 1, wherein the one or more mineral UV filtering agents are selected from titanium dioxide, zinc oxide, iron oxides, cerium oxides, zirconium oxides, and a mixture thereof.

18. The composition of claim 17, wherein the one or more mineral UV filtering agents is present from about 1 to about 25 wt. % based on the total weight of the composition.

19. The composition of claim 1, wherein the ratio between the cationic surfactant and the total amount of oil thickening agents is from about 0.1 to about 2.8.

20. A composition in the form of a water-in-oil emulsion comprising:
   a. from about 0.1 to about 3 wt. % of a cationic surfactant;
   b. from about 0.5 to about 4 wt. % of one or more oil thickening agent;
   c. from about 0.5 to about 4 wt. % of one or more non-silicone treated pigments;
   d. one or more mineral UV filtering agents;
   e. one or more fillers;
   f. a water phase of about 28 to about 50 wt. % of water;
   g. one or more emulsifiers; and
      wherein the ratio between the cationic surfactant and the total amount of oil thickening agents is from about 0.05 to about 3; and
      wherein the weight percentages are based on the total weight of the composition.

21. A method for protecting skin from UV radiation comprising applying an effective amount of the composition of claim 1 to the skin.

* * * * *